(12) United States Patent
Van Wyck

(10) Patent No.: US 10,014,075 B2
(45) Date of Patent: Jul. 3, 2018

(54) SYSTEM FOR ENCOURAGING HEALTH SUPPORT PROGRAM PARTICIPATION

(71) Applicant: William J Van Wyck, Darien, CT (US)

(72) Inventor: William J Van Wyck, Darien, CT (US)

(73) Assignee: Zillion Group, Inc., Norwalk, CT (US)

( * ) Notice: Subject to any disclaimer, the term of this patent is extended or adjusted under 35 U.S.C. 154(b) by 931 days.

(21) Appl. No.: 14/025,454

(22) Filed: Sep. 12, 2013

(65) Prior Publication Data
US 2014/0074498 A1  Mar. 13, 2014

Related U.S. Application Data

(60) Provisional application No. 61/700,082, filed on Sep. 12, 2012.

(51) Int. Cl.
*G16H 10/60* (2018.01)
*G06Q 30/02* (2012.01)

(52) U.S. Cl.
CPC ......... *G16H 10/60* (2018.01); *G06Q 30/0207* (2013.01); *G06Q 30/0226* (2013.01)

(58) Field of Classification Search
CPC .... G06Q 50/22; G06Q 30/02; G06Q 30/0251; G06Q 30/0207; G06Q 50/24; G06Q 30/0269; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | | |
|---|---|---|---|---|
| 5,363,955 A | * | 11/1994 | Fleenor | B65D 5/422 206/268 |
| 7,711,580 B1 | * | 5/2010 | Hudson | G06F 19/322 434/322 |
| 2004/0193489 A1 | * | 9/2004 | Boyd | G06Q 30/02 713/176 |
| 2005/0059034 A1 | * | 3/2005 | Tyler | G06F 19/28 435/6.18 |
| 2005/0224387 A1 | * | 10/2005 | Desjardins | G09F 1/02 206/527 |
| 2007/0067188 A1 | * | 3/2007 | McDevitt | G06Q 10/10 705/2 |

(Continued)

*Primary Examiner* — Joseph D Burgess
(74) *Attorney, Agent, or Firm* — Boyle Fredrickson, SC

(57) ABSTRACT

A value icon for a web-based health or health support program packages access information for a website in a value icon physically embodying the abstract benefits of the welfare program in order to encourage initial access of the health support website. The value icon may be a compact container holding a three-dimensional article having a health support-related utility, at least one printed coupon representing a healthcare program credit and may provide the address to a health support website which offers additional programs based on information from an individual in a questionnaire on the health support website.

6 Claims, 3 Drawing Sheets

(56) References Cited

U.S. PATENT DOCUMENTS

| | | | |
|---|---|---|---|
| 2007/0106538 A1* | 5/2007 | Holtermann | G06Q 40/08 705/4 |
| 2007/0205118 A1* | 9/2007 | Westendorf | B44C 1/105 206/229 |
| 2011/0020772 A1* | 1/2011 | Carter | A47G 23/10 434/127 |
| 2013/0346216 A1* | 12/2013 | Black | G06Q 10/00 705/14.66 |

* cited by examiner

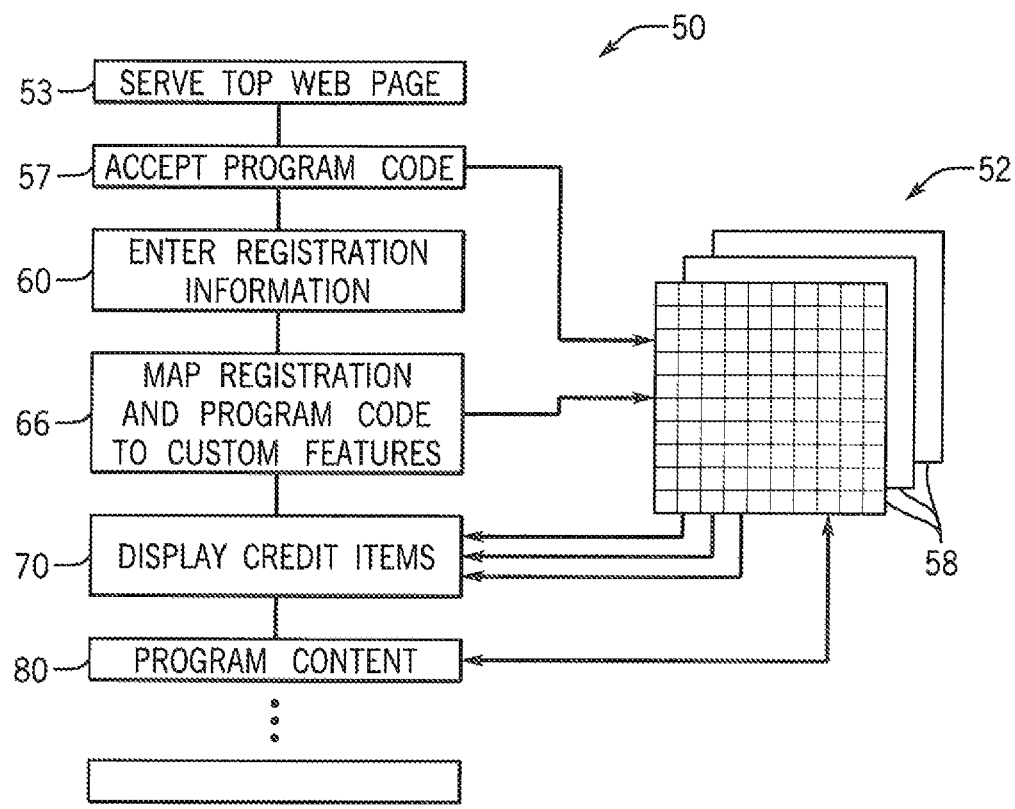

SYSTEM FOR ENCOURAGING HEALTH SUPPORT PROGRAM PARTICIPATION

CROSS REFERENCE TO RELATED APPLICATION

This application claims the benefit of U.S. provisional application 61/700,082 filed Sep. 12, 2012 and hereby Incorporated by reference.

BACKGROUND OF THE INVENTION

The present invention relates to a method for administering health support programs and in particular to a method to increase participation in a web-based health, support program.

SUMMARY OF THE INVENTION

Encouraging patients to take active steps to improving their own health is difficult. In order to promote such engagement, it is understood that health support programs should be tailored to the individual patient in a way that is relevant to the patient's condition and lifestyle. One way of doing this is to have the individual go to a website and respond to questions about his or herself. A computer program operating on the data from the website questionnaire may then provide tailored information and programs to the patient including documents, web accessible programming, and access to human specialists.

The approach of using a web-based questionnaire that may be filled out by the patient overcomes many of the problems related to confidentiality with respect to existing medical records, such problems which prevent an employer, for example, from providing health information directly to the health support program administrator.

Unfortunately, this first step of having the patient visit the website and answer a health questionnaire can be the downfall of such approaches. As few as six percent of patients presented information about a web page based healthcare program actually visit the web page.

SUMMARY OF THE INVENTION

The present invention provides a way to dramatically boost the number of people who take the first step of visiting the website of a web-based health support program. Generally the invention provides a "value icon" that can be given to an individual that provides a tangible representation of the benefits that the patient will achieve by visiting the web page even before the benefits have been personalized to the patient. The value icon may include a mixture of instructions for use, printed coupons and a three-dimensional article with a health support-related utility (such as a tape measure or blood lancet) all contained in a gift-sized box consistent with an individual's experiences of value. The outer surface of the value icon may include common indicia of value including a printed price, UPC code and the like.

Specifically, the invention provides a value icon for a health support program having a sealable container holding a three-dimensional article with a health support-related utility, and at least one printed coupon representing a healthcare program credit. The container provides an address to a website linking the healthcare program credit to a specific healthcare program based on information from an individual receiving the value icon entered into the website.

It is thus one feature of at least one embodiment of the invention to provide a compact and generalizable value icon that can be distributed to individuals regardless of their health support needs that will evoke a sense of received value to encourage participation with the web-based health support program.

The three-dimensional article may be selected from the group consisting of a tape measure, a pedometer, a flexible stress reliever, blood lancet, a pill splitter, and a pill box.

It is thus one feature of at least one embodiment of the invention to provide a compact article of perceived value and utility related to health support.

The three-dimensional article is a tape measure and wherein the information from the individual is body measurements made with the tape measure of the individual.

It is thus one feature of at least one embodiment of the invention to provide a representation of value that can assist an individual in personalizing the health support program to the individual by allowing body measurements to be entered into the website questionnaire.

The container may have a description of a health support program printed on its outer surface.

It is thus one feature of at least one embodiment of the invention to begin the process of education of the individual and how to access the website immediately upon the receipt of the value icon.

The container may have a price printed on its outside denoting a value of over 100 dollars and/or may have a UPC code printed on its outer surface It is thus one feature of at least one embodiment of the invention to leverage symbols ordinarily associated with value.

The container may provide a printed list of steps for the individual to complete to visit the website to link the healthcare program credit to a specific healthcare program visible immediately upon opening the container without removal of items in the container.

It is thus one feature of at least one embodiment of the invention to provide instructions to the user for accessing the website that are likely to be retained by the user during the time between receipt of the value icon and the accessibility of the web to the user.

The container may have a volume of substantially twelve cubic inches, and may for example, be a cubic cardboard box.

It is thus one feature of at least one embodiment of the invention to mimic a gift box of the type that would hold a valuable gift such as jewelry or the like.

The contents of the container may be positioned in layers which must be successively removed to access the contents of the container and wherein the three-dimensional article having a health support-related utility is positioned in a layer below at least one printed coupon and wherein the address to a website is visible before removing the three-dimensional article or coupons.

It is thus one feature of at least one embodiment of the invention to encourage exploration of all of the elements of the value icon by the user.

The value icon may include a code number enterable by the individual at the website and visible before removing the three-dimensional article or coupons.

It is thus one feature of at least one embodiment of the invention to allow differentiation of a health support program not only by an individual's needs but also by an individual's affiliation with a particular institution or place of work such as may be captured in the code number.

These particular objects and advantages may apply to only some embodiments falling within the claims and thus do not define the scope of the invention.

BRIEF DESCRIPTION OF THE DRAWINGS

FIG. 4 is a flowchart of a program executable on the computer server as may access an associated database;

FIG. 5 is a simplified screenshot of a first web page visible to the consumer/participant accessing the web-based health support program in which registration numbers may be entered;

FIG. 6 is a figure similar to that of FIG. 5 showing a menu page available to the individual after registration providing a link to a questionnaire;

DETAILED DESCRIPTION OF THE PREFERRED EMBODIMENT

Figure 1:
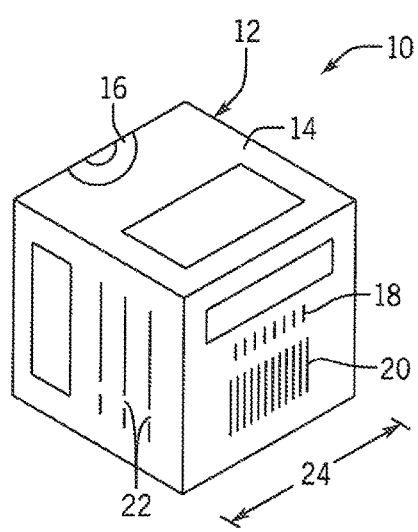
FIG. 1 is a perspective view of a value icon per the present invention before being opened by a consumer/participant such as presents a small box with descriptive elements and indicia of value printed on its outer surface.

Referring now to FIG. 1, a value icon 10 may provide generally for a cubic cardboard box 12 having an upper flap 14 hingably openable to permit access to the contents of the box 12 yet sealed by a seal 16 during initial presentation.

The box 12 may include outer printed indicia 18 providing a numeric value indicating a price of the box (e.g. $189) and a UPC code such as are found on many products offered for sale to consumers. A description 22 of the health support program may also be provided on the outer surfaces of the box 12 summarizing the health support program benefits, listing necessary computer equipment for the program, and indicating a prepayment by an institution such as a place of employment of the consumer/participant for these health support program benefits.

In one embodiment, the box 12 is sized to approximate a jewelry or other small gift box and may have a side dimension 24 for example, of substantially 2¼ inches and/or may have a volume of substantially twelve cubic inches and may be fabricated of cardboard.

Figure 2:
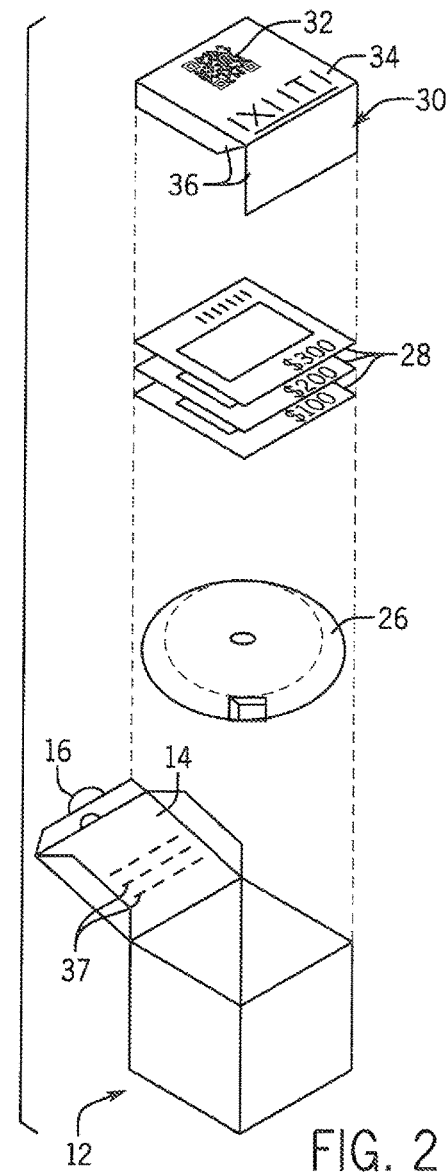
FIG. 2 an exploded view of the value icon of FIG. 1 showing the box as opened and its contents including an instruction card with registration information, coupons, and a health support-related article of utility.

Referring now to FIG. 2, when the upper flap 14 is opened after removing or separating the seal 16, the contents of the box 12 may be removed. In one embodiment, a lowermost item in the box 12 may be a three-dimensional article 26 having a health support related utility. In a preferred embodiment, the three-dimensional article 26 will be a tape measure; however, other articles may be contemplated such as a pedometer, a flexible stress reliever, blood lancet, a pill splitter, and a pillbox, each that represent items likely to have genuine utility to the consumer/participant related to health support.

Positioned above the article 26 may be one or more static or dynamic coupons 28 each, for example, being a generally square printable paper slip identifying a dollar or other benefit value to the consumer/participant. The static coupons 28 may be specifically identified to a benefit whereas the specific benefit of the dynamic coupons will be identified later. Dollar values and or pre-conditions of the coupons may be listed.

Above the coupons 28 may be an instruction card 30 providing address information 32 for the health support website and a registration code 34. The address information 32 may be in the form of a printed address (for example www.healthfleet.com) or the same information contained in a QR or similar code readable by a computer connected camera, smart phone or the like. The registration code 34 will, typically be unique to an institution or group but not to an individual. In this way, the boxes 12 can be preloaded and sealed and given to any employee in a group meeting. Instruction card 30 may include downwardly extending flaps 36 to help corral and organize the other materials and prevent the instruction card 30 from being lost or discarded accidentally. Alternatively or in addition, the address information 32 and the registration code 34 may be attached directly to the box 12 by a sticker or the like so as to be better retained.

Instructions 37 for using the contents of the box 12 to access the health support-based Web program may be printed inside the flap 14. These instructions will be identical for all groups and all individuals.

Figure 3:
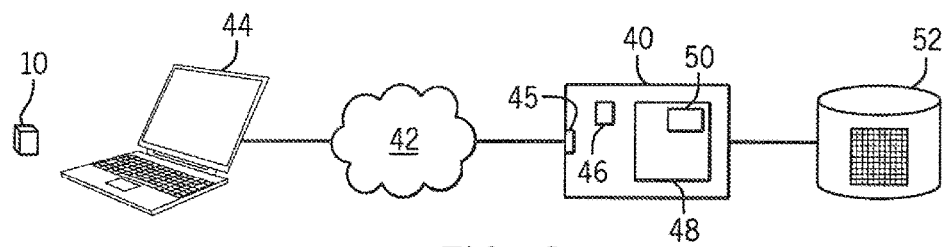
FIG. 3 is a simplified representation of a computer system providing a web-based health support program suitable for use with the present invention, including a computer server accessible over the Internet by the consumer/participant through a home computer.

Referring now to FIG. 3, the value icon 10 may be used by a consumer/participant to access a web-based health support program implemented by one or more servers 40 connected through the Internet 42 with a consumer/participant's personal computer 44 or the like, including a desktop personal computer, a tablet computer, smart phone, or other computing device that is web accessible. The server 40 may include a network interface element 45 as is generally understood in the art connected to an electronic processor 46. The electronic processor 46, in turn may be in communication with an electronic memory 48 providing a non-transient storage medium for holding one or more programs 50 implementing a web portion of the present invention. The memory 48 may generally include random access memory, or the like as well as disk memory, the latter which may hold a database 52 storing information about the consumer/participant that may be used for personalizing the health support program as will be described.

Referring now to FIGS. 4 and 5, the program 50 may respond to a consumer/participant entering the website address into a browser (the address provided by the above described address information 32) by serving a top-level web page 51 indicated by process block 53. This top-level web page 51 may provide, for example, welcome information and a visual image 54 showing the location of the registration code on the instruction card 30 together with instructions for entering that registration code in a text box 56.

The process of accepting the registration code as entered by the consumer/participant, as indicated by process block 57, identifies a group page 58 in the database 52 providing information related to the desired health support program by a particular institution.

Referring now to FIGS. 4 and 6, the information from the group page 58 may be used to generate a directory screen 59 providing a profile link 60, a questionnaire link 62, and a program link 64, the latter which can be accessed only after completion of the profile and questionnaire.

Generally, following the profile link 60 will lead the consumer/participant to a page where they may enter personally identifying information that will be used to allow them to access personalized information on the website. This personally identifying information may include a participant name that may be linked to a particular record of the group page 58 and that may be used to confirm that the consumer/participant is properly part of the group identified by the registration code 34. The personally identifying information may further include a consumer/participant selected personal identification number and/or password combination.

The questionnaire accessible through the questionnaire link 62 will include a questionnaire for the entry of health information by the consumer/participant. In particular this health information may include body measurements made with the tape measure of the article 26 including height, waist size and other body dimensions which may be used to personalize the health support program. By having the consumer/participant enter this information, problems of transfer of sensitive health information from an employer or the like is largely eliminated. Other medical information including gender, age, known ailments, medications, and the like may also be entered into this questionnaire.

As indicated by process block 66, this information may be used to tailor a health support program to the particular consumer/participant's needs according to a simple mapping program which may characterize each consumer/participant according to a cluster or range of information entered into the questionnaire. For example, consumer/participants with certain ratios of height to waist size may be steered toward particular nutrition programs either for losing or gaining weight. Age information may be used to affect nutrition suggestions or exercise programs and the like.

This customize health support program may then be accessed by the program link 64.

Figure 7:
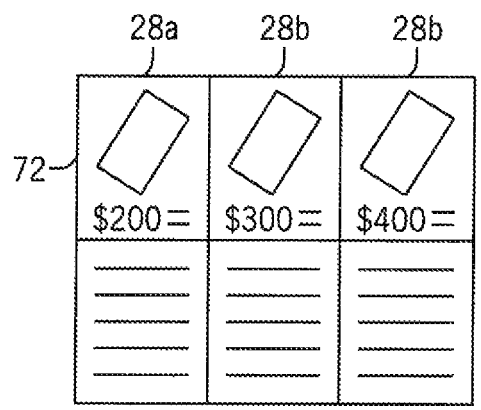
FIG. 7 is a figure similar to that of FIGS. 5 and 6 showing a representation of dynamic coupons personalized to the consumer/participant based on questionnaire information.
Figure 8A:
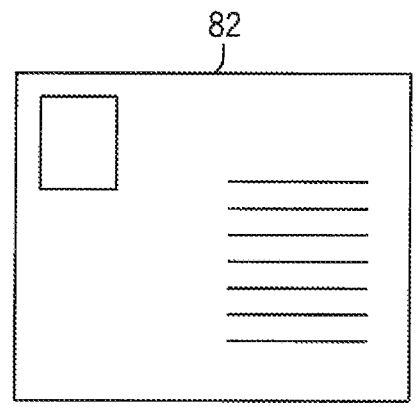
FIGS. 8a-8c are screen shots of web-based health support programming that may be provided to the consumer/participant based on data entered from the questionnaire including personalized health programs, health risk management tools, access to live expert counseling, and risk, assessment tools.
Figure 8B:
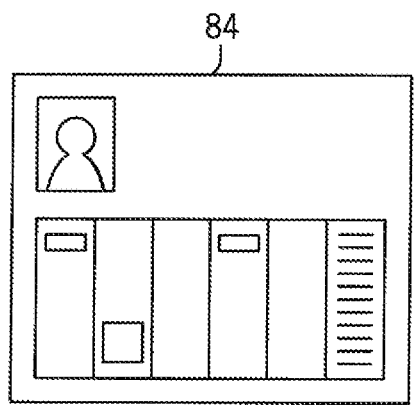
Figure 8C:
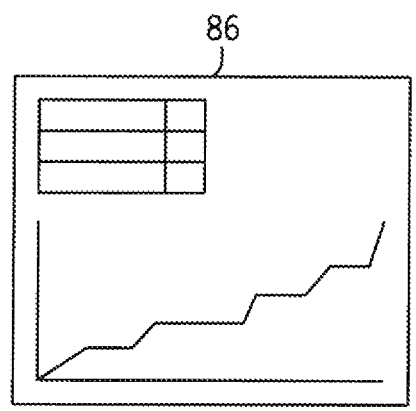

Referring now to FIGS. 4 and 7, access by the consumer/participant of the program page from the program link 64, as indicated by decision block 70, may present a coupon screen 72 as shown in FIG. 7. This coupon screen may display representations the coupons 28 including static coupons 28a whose value and purpose is fully explained in the physical coupon 28 and dynamic coupons 28b whose values and purpose are dynamically populated based on entries from the health questionnaire. For example, static coupons 28 may provide for a fitness club membership that would be applicable to most consumer/participants. Dynamic coupons 28 may, for example, provide discounts on supplements or equipment that would be applicable to specific consumer/participants, for example vitamins keyed to a gender of the consumer/participant or coupons to particular programs, for example smoking cessation or stress reduction, that might be applicable to consumer/participants. The particular benefit provided by dynamic coupons 28 may be populated into the images of those dynamic coupons.

One of the dynamic or static coupons may allow the recipient to take the coupon to a local screening facility (Walgreens, Quest, etc.) to have a blood screening, blood pressure test, or the like taken on-site. Then those results can be then displayed to the user securely within the health portal. This reliable data that will allow the program provider to measure the effect of the program over time without having to rely on subjective or self-reported information by the user/patient. This approach can also be used for a mail-in blood lancet where the results could be posted directly by the testing facility.

Referring now to FIG. 4 and FIGS. 8a-e, the program page accessed through the program link 64 will also allow the consumer/participant access to a variety of web-based health support content including, for example, information screens 82 providing text, image and/or video information about health to the consumer/participant. Such information screens 82 can also provide for calculators and other health support tools that can be delivered over the web.

Alternatively, the consumer/participant may access portal screens 84, for example, providing access to health or health support specialists who can confer with the consumer/participant individually or in a group. The consumer/participant may use these portal screens 84 to schedule sessions with the health or health support specialists.

Alternatively the consumer/participant may access tracking screens 86 which allow the consumer/participant to track his or her progress with respect particular health support programs by entering data and aggregating data from other sources in the form of a personal health record.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer", "a processor" or the like can be understood to include one or more processors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What I claim is:

1. A health support program system comprising:
    (a) a plurality of value icons each having:
    a sealable container; and
    received within the container:
        (i) a three-dimensional article having a health support-related utility, the three-dimensional article being configured to allow a consumer/participant to obtain a body measurement;
        (ii) at least one printed coupon representing a healthcare program credit; and
        (iii) a registration code enterable by an individual at a website;
    wherein the container provides an address to the website, and
    wherein the registration code is unique to a group but not to an individual; and
    (b) an electronic computer communicating with the Internet and executing a program stored in non-transient medium to implement a web page for accepting the registration code to identify a group page for the group,
    wherein the group page identifies a profile link and a questionnaire,
    wherein the profile link provides a page which receives personally identifying information to allow access to pages including personalized information,
    wherein the personally identifying information is used to confirm that the consumer/participant is part of the group identified by the registration code, and
    wherein the questionnaire receives answers, including the body measurement obtained from the three-dimensional article, to link the healthcare program credit to a specific healthcare program.

2. The health support system of claim 1 wherein the three-dimensional article is a tape measure and the questionnaire solicits information obtained by measurement of a consumer/participant by the tape measure.

3. The health support system of claim 1 wherein the specific health programs are selected from healthcare programs related to different aspects of health related to different specialties.

4. The health support system of claim 1 wherein the registration code identifies a consumer/participant to a variety of different consumer/participant groups associated with different healthcare programs.

5. The health support system of claim 1 wherein the registration code is on an instruction card, and wherein the electronic computer further executes to display a visual image showing a location of the registration code on the instruction card.

6. The health support system of claim 1 wherein the personally identifying information includes a name of the consumer/participant that is linked to a particular record of the group page.

* * * * *